US012343086B2

(12) United States Patent
Holm et al.

(10) Patent No.: US 12,343,086 B2
(45) Date of Patent: Jul. 1, 2025

(54) SYSTEM AND METHOD FOR IMPLANTING LEFT VENTRICULAR ASSIST DEVICES

(71) Applicant: Regents of the University of Minnesota, Minneapolis, MN (US)

(72) Inventors: Mikayle Ashlyn Holm, Minneapolis, MN (US); David Alfonso Ramirez, St Paul, MN (US); Paul Anthony Iaizzo, White Bear Lake, MN (US); Andrew W. Shaffer, Minneapolis, MN (US); Anthony Robert Prisco, Lakeville, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 640 days.

(21) Appl. No.: 17/491,175

(22) Filed: Sep. 30, 2021

(65) Prior Publication Data
US 2022/0104879 A1    Apr. 7, 2022

Related U.S. Application Data

(60) Provisional application No. 63/198,196, filed on Oct. 2, 2020.

(51) Int. Cl.
| *A61B 34/10* | (2016.01) |
| *A61M 60/178* | (2021.01) |
| *A61M 60/861* | (2021.01) |
| *G06T 17/00* | (2006.01) |
| *G16H 20/40* | (2018.01) |

(Continued)

(52) U.S. Cl.
CPC .......... *A61B 34/10* (2016.02); *A61M 60/178* (2021.01); *A61M 60/861* (2021.01); *G06T 17/00* (2013.01); *G16H 20/40* (2018.01); *G16H 30/20* (2018.01); *G16H 30/40* (2018.01); *G16H 50/50* (2018.01);
(Continued)

(58) Field of Classification Search
CPC .............. A61B 34/10; A61B 2034/105; A61B 2034/107; A61M 60/178; A61M 60/861; G06T 17/00; G06T 2210/41; G16H 20/40; G16H 30/20; G16H 30/40; G16H 50/50
See application file for complete search history.

(56) References Cited

U.S. PATENT DOCUMENTS

| 8,682,626 B2 | 3/2014 | Ionasec et al. |
| 10,368,878 B2 | 8/2019 | Lavallee et al. |

(Continued)

FOREIGN PATENT DOCUMENTS

| CA | 2992648 A1 | 7/2019 |
| WO | 2011046425 A2 | 4/2011 |

OTHER PUBLICATIONS

Collin, Sophie. Preoperative planning and simulation for artificial heart implantation surgery. Diss. Université de Rennes, 2018. (Year: 2018).*

(Continued)

*Primary Examiner* — Sean D Mattson
(74) *Attorney, Agent, or Firm* — Shumaker & Sieffert, P.A.

(57) ABSTRACT

A system and method for implanting heart assist devices. A model of a heart of a patient is formed based on images taken of the cardiothoracic cavity of the patient. A point is selected for insertion of the heart assist device based on the model. A graft location is selected on the aorta and a graft length for the graft is determined as a function of the implant location and the selected graft location.

15 Claims, 13 Drawing Sheets

(51) Int. Cl.
    *G16H 30/20*     (2018.01)
    *G16H 30/40*     (2018.01)
    *G16H 50/50*     (2018.01)

(52) U.S. Cl.
    CPC ... *A61B 2034/105* (2016.02); *A61B 2034/107* (2016.02); *G06T 2210/41* (2013.01)

(56) References Cited

U.S. PATENT DOCUMENTS

| | | | |
|---|---|---|---|
| 2004/0009459 | A1 | 1/2004 | Anderson et al. |
| 2007/0112325 | A1* | 5/2007 | Wieselthaler ....... A61M 60/178 604/500 |
| 2012/0022843 | A1 | 1/2012 | Ionasec et al. |
| 2014/0148693 | A1 | 5/2014 | Taylor |
| 2019/0298904 | A1* | 10/2019 | Pya ................... A61B 17/0482 |
| 2023/0157755 | A1* | 5/2023 | Kim ...................... G16H 50/20 382/130 |

OTHER PUBLICATIONS

Zhong, Liang, et al. "Left ventricular regional wall curvedness and wall stress in patients with ischemic dilated cardiomyopathy." American Journal of Physiology-Heart and Circulatory Physiology 296.3 (2009): H573-H584. (Year: 2009).*

Mazzitelli, Rosario, et al. "Numerical prediction of the effect of aortic Left Ventricular Assist Device outflow-graft anastomosis location." Biocybernetics and Biomedical Engineering 36.2 (2016): 327-343. (Year: 2016).*

Aliseda et al., "LVAD Outflow Graft Angle and Thrombosis Risk," Asaio J., vol. 63, No. 1, Jan. 2017, 25 pp.

Anselmi, MD, PhD et al., "Virtual implantation and patient-specific simulation for optimization of outcomes in ventricular assist device recipients," Medical Hypotheses, vol. 91, Jun. 2016, pp. 67-72.

Anselmi, MD, PhD et al., "Virtual implantation of a novel LVAD: toward computer-assisted surgery for heart failure," ScienceDirect, Journal of Surgical Research, Sep. 2016, pp. 204-207.

Cohn et al., "Reinforcement of Left Ventricular Assist Device Outflow Grafts to Prevent Kinking," Ann. Thorac. Surg., vol. 84, No. 1, Jul. 1, 2007, 5 pp.

Gross et al., "Continuous LVAD monitoring reveals high suction rates in clinically stable outpatients", Artificial Organs, vol. 44, No. 7, Jul. 2020, pp. E251-E262.

Hanke et al., "Minimally-invasive LVAD Implantation: State of the Art." Curr Cardiol Rev, Aug. 2015, jpp. 246-251.

Holm, Computational assessments of the ideal insertion sites for transapical procedures, European Society of Cardiothoracic Surgeons, Oct. 5, 2019, 20 pp.

Holm, et al., "Computationally determining ideal insertion site for transapical procedures," European Society of Cardiothoracic Surgeons, Oct. 5, 2019, 1 pp.

Honjo, MN, PhD, "Implantation of HeartWare Left Ventricular Assist Device in Pediatric Population," Operative Techniques in Thoracic and Cardiovascular Surgery, vol. 19, Issue 1, Mar. 2014, 34 pp.

Lozinski "Hybrid Multi-Objective Optimization of Left Ventricular Assist Device Outflow Graft Anastomosis Orientation to Minimize Stroke Rate," Dec. 2019, 108 pp.

Makdisi et al., "Minimally Invasive Is the Future of Left Ventricular Assist Device Implantation," J Thorac Dis, Sep. 2015, pp. E283-E288.

Mancini, MD et al. "Left ventricular assist devices: A rapidly evolving alternative to transplant," J. Am. Coll. Cardiol., vol. 65, No. 23, Jun. 16, 2015, pp. 2542-2555.

Marsden et al., "Recent advances in computation methodology for simulation of mechanical circulatory assist devices," Wiley Interdiscip Rev Syst Biol Med, Mar. 2014, pp. 169-188.

Muslem et al., "Kinking, thrombosis and need for re-operation in a patient with a left ventricular assist device", Intensive Care Medicine, vol. 42, No. 12, Dec. 2016, pp. 2090-2091.

Osorio et al., "Computational Fluid Dynamics Analysis of Surgical Adjustment of Left Ventricular Assist Device Implantation to Minimize Stroke Risk," 31 pp.

Pauls et al., "Evaluation of physiological control systems for rotary left ventricular assist devices: an in-vitro study", Annals of biomedical engineering, Aug. 2016, pp. 2377-2387.

Peng et al., "Modeling of a New Sensorless Suction Detection System for the Rotary Left Ventricular Assist Device", In 2018 9th International Conference on Information Technology in Medicine and Education (ITME), Oct. 19, 2018, pp. 247-251.

Petrou et al., "Standardized comparison of selected physiological controllers for rotary blood pumps: in vitro study", Artificial organs, vol. 42, No. 3, Mar. 28, 2018, pp. E29-E42.

Prather "Multi-Scale Fluid-Structure Interaction Model Analysis of Patient-Specific Geometry for Optimization of LVAD Outflow Graft Implantation: An Investigation Aimed at Reducing Stroke Risk," May 2018, 182 pp.

Ramirez et al., "Computationally sizing a left ventricular assist device graft: A pre-procedural tool to improve surgical outcomes", Proceedings of the 2020 Design of Medical Devices Conference, Minneapolis, MN, USA, Apr. 6, 2020, p. 3.

Sen et al., "Mechanical circulatory assist devices: a primer for critical care and emergency physicians" Critical Care, Jun. 25, 2016, 20 pp.

Stulak, MD et al., "Implantation of a Durable Left Ventricular Assist Device: How I Teach It," The Annals of Thoracic Surgery, vol. 103, issue 5, Jun. 1, 2017, pp. 1687-1692.

Terzic et al., "Kinking of the Outflow Graft, Consequent Ventricular Tachycardia, and the Need for Reoperation in a Patient with Left Ventricular Assist Device", In the Heart Surgery Forum, vol. 20, No. 4, Aug. 24, 2017, pp. E139-E141.

Whitson, "Surgical Implant Techniques of Left Ventricular Assist Devices: An Overview of Acute and Durable Devices," J Thorac Dis, Dec. 2015, pp. 2097-2101.

Wood et al., "Survival outcomes of stenting outflow graft stenosis in continuous-flow left ventricular assist devices: a systematic review", Heart Failure Reviews, vol. 25, No. 6, Nov. 2020, pp. 985-992.

\* cited by examiner

SYSTEM AND METHOD FOR IMPLANTING LEFT VENTRICULAR ASSIST DEVICES

This application claims the benefit of U.S. Provisional Application No. 63/198,196, filed Oct. 2, 2020, the entire content of which is herein incorporated by reference.

BACKGROUND

For some patients with end stage-heart failure, one option for survival is the implantation of a left ventricular assist device (LVAD) for providing mechanical circulatory support. Such a device decreases the workload on the diseased heart and increases survivability, thus providing a bridge to a critical medical decision, a bridge to transplant, or a bridge to recovery. Such a device may also be used as a destination therapy.

LVAD implantation can, however, be very complex and unforgiving given the expected longevity of the device inside the body and the internal movements of the thorax. While the technological advancements in the machinery involved continues to improve, the surgical procedure has been relatively unchanged throughout, with little movement to minimally invasive approaches. Given the seriousness of complications, improvements on these procedures should be explored.

One source off chronic problems in LVAD implantation lies in the blood flow from the pump to the aorta. This flow is carried commonly by a corrugated graft that is sized and cut during implantation. The sizing of this graft is typically done by placing this tubing over the patient's body and estimating the relative length needed to extend from the outflow of the LVAD pump to the attachment site on the ascending aorta.

A mismatch of the graft length versus the actual anatomical distance of the path around the heart may result in a less than ideal implantation procedure. For example, if the graft is too long, it is susceptible to kinking and possible obstruction of blood flow, increasing the risk of clotting and leading to the LVAD providing less assistance than intended. If the outflow graft is too short, however, the graft may cross over the anterior surface of the heart and put undue pressure on the right ventricle, leading to future complications with the graft or/and to right-sided heart issues.

SUMMARY

Left Ventricular Assist Devices (LVADs) are implantable mechanical pumps that augment the pumping ability of a patient's heart. The following disclosure describes ways of making the implantation of LVADs mode reliable and reproducable.

The disclosure describes methods for determining where an LVAD should connect to the heart, where an outgoing graft from the LVAD should connect to the aorta, the length of the outgoing graft, the bevel angle for the graft connection to the aorta, and the placement of the LVAD within the chest. The disclosure also describes a method for connecting a graft to a blood vessel to minimize turbulence in the combined blood flow.

In one example, a method of planning implantation of a heart assist device, the method including accessing images of the cardiothoracic cavity of a patient; forming, based on the images, a model of the heart of the patient, the model including a model of a mitral valve annulus; identifying an apical region; and selecting an insertion point for implanting the heart assist device within the apical region.

In another example, a method of determining the length of a graft used for implanting a left ventricular assist device (LVAD) in a patient, the method including accessing images of the cardiothoracic cavity of the patient; forming a model of the heart of the patient; determining an implant location; selecting a graft location on the aorta; and calculating the graft length as a function of the implant location and the selected graft location.

In another example, a system includes memory and one or more processors connected to the memory, wherein the memory includes instructions that, when executed by the one or more processors, cause the system to access images of the cardiothoracic cavity of a patient; form, based on the images, a model of the heart of the patient, the model including a model of a mitral valve annulus; and select an insertion point for the heart assist device based on the model.

In yet another example, a system includes memory and one or more processors connected to the memory, wherein the memory includes instructions that, when executed by the one or more processors, cause the system to access images of the cardiothoracic cavity of a patient; form, based on the images, a model of the heart of the patient; select an insertion point for the heart assist device based on the model; select a graft location on the aorta; and calculate a graft length as a function of the implant location and the selected graft location.

The details of one or more aspects of the disclosure are set forth in the accompanying drawings, the description below and the attached appendix. Other features, objects, and advantages of the techniques described in this disclosure will be apparent from the description, drawings, and claims.

BRIEF DESCRIPTION OF THE DRAWINGS

Like reference characters refer to like elements throughout the figures and description.

DETAILED DESCRIPTION

Figure 1:
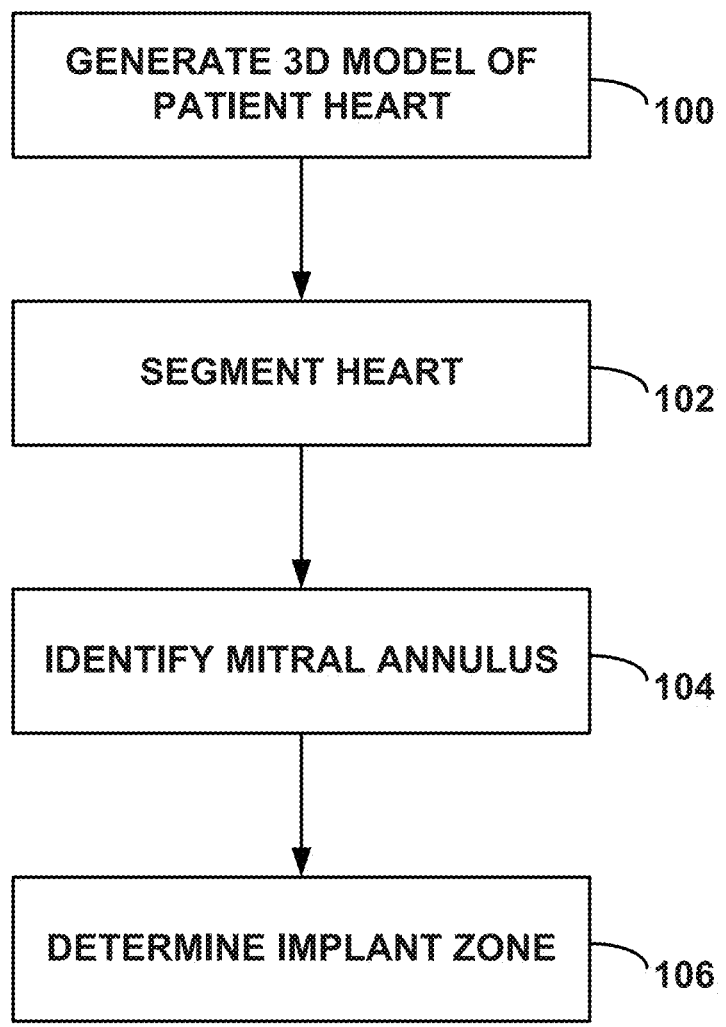
FIG. 1 is a block diagram illustrating a method of determining a LVAD pump implant location, according to one aspect of the disclosure.

Left Ventricular Assist Devices (LVADs) are routinely used to provide life-saving support to patients in end-stage heart failure. If the device is not implanted properly, however, the life-saving therapy may be associated with serious clinical complications and even death. Importantly, the graft that carries the blood from the LVAD pump to the aorta needs to be sized to not cause any compounding complications. What is described is a technique that utilizes pre-procedural or intra-procedural imaging to better determine the personalized, near ideal, length of the LVAD graft.

The LVAD pumps blood from the left ventricle to the aorta, bypassing the aortic valve. In operation, blood flows from the left ventricle into the pump of the LVAD and then through connecting tubing, i.e., the graft, to the aorta. Left ventricular assist devices (LVADs) can be lifesaving therapies that improve life expectancy for the patients that receive it. As noted above, the target patient population often suffers from end-stage heart failure and may therefore be susceptible to morbidities arising from a less than ideal surgical implantation. Importantly, the graft that carries the blood from the LVAD pump to the aorta needs to be placed and sized to avoid compounding complications. In one approach, the graft is placed to circumvent the heart on the outside perimeter of the right ventricle.

Typically, a surgeon determines the placement of the LVAD during surgery, cutting the graft as necessary to install the device. As every patient is different, a surgeon essentially "eyeballs" where to place the device during an operation and trims the graft while taking very few measurements. Such an approach may lead to problems. As noted above, if the graft length is too long, the graft may kink. A kink in the graft may lead to turbulent blood flow, potentially damaging the blood cells. If too short, the graft may press on the right ventricle, compressing the right coronary artery and interfering with the expansion and contraction of the right ventricle.

Furthermore, the operation to implant an LVAD is complicated and may be physically demanding. Patients who may benefit from such surgeries are typically on cardiac bypass; the process requires the surgeon to twist the heart to access the right area while determining an implantation location for the LVAD and the optimal graft length. At the same time, as noted above, patients may receive the life saving device implant, but later have complications or even die because of issues with how the device was implanted. The techniques described herein reduce device related complications since the implant is made in a more calculated and patient-specific manner.

In one example approach, the computational tool uses pre-procedural or intra-procedural imaging to form a model of the patient's heart. In one such example approach, CT imaging is coupled with contrast for intra-procedural imaging. In another such example approach, MRI scans of a patient's heart are taken as part of pre-procedural imaging. Other imaging modalities (e.g., ultrasound techniques such as transthoracic and transesophageal echo and fluoroscopy) may be used as well. The tool then employs virtual segmentation to appropriately measure the length from the LV apex, the ideal pump implant location, to the ascending aorta. For instance, pre-procedural MRI images may be used to computationally determine the apical region most perpendicular to the mitral valve annulus. Such approaches address the problems noted above; they should lead to fewer complications and thus a higher success rate for LVAD implantations.

FIG. 1 is a block diagram illustrating a method of determining a LVAD pump implant location, according to one aspect of the disclosure. In the example shown in FIG. 1, images of a heart are imported and used to generate a three-dimensional model of a patient's heart (100). The heart, mitral valve and apical dimple are segmented within the image (102) and the mitral valve annulus identified (104). The implant zone is then determined with respect to the mitral valve annulus (106).

Figure 2:
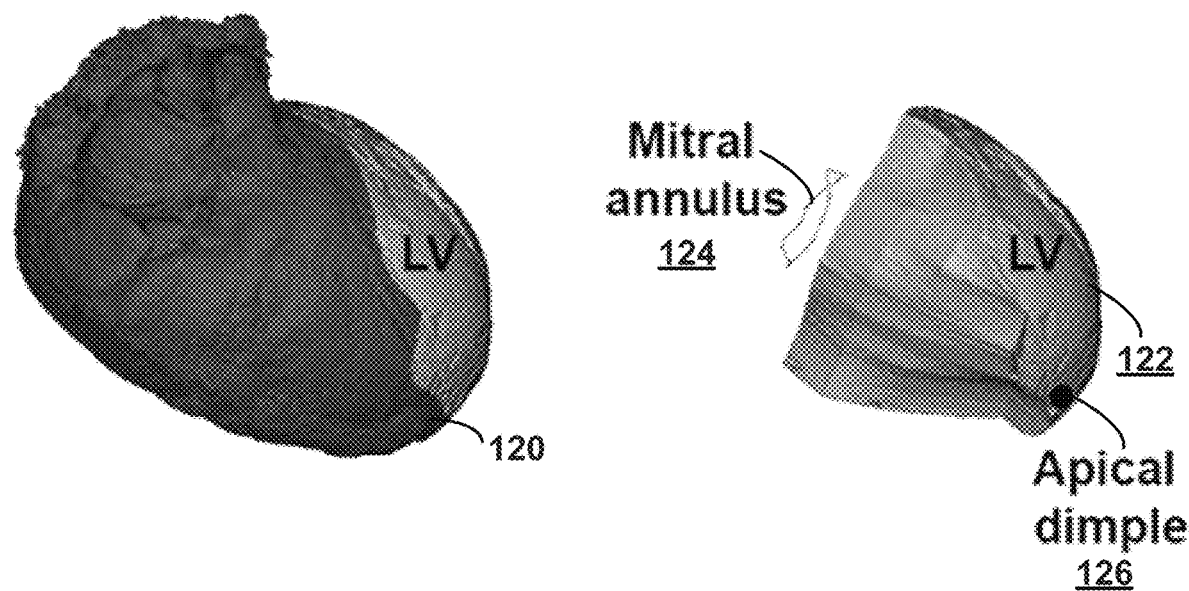
FIG. 2 illustrates a segmented three-dimensional (3D) model of a heart, according to one aspect of the disclosure.

FIG. 2 illustrates a segmented three-dimensional (3D) model of a heart, according to one aspect of the disclosure. In the example shown in FIG. 2, heart 120 has been segmented to illustrate the left ventricle 122, the mitral valve annulus 124 and the apical dimple 126. The heart 120, mitral valve annulus 124, and apical dimple 126 may be segmented from, for instance, images captured in a chest CT scan and imported into the computational tool. In one example approach, the most effective implant zone is where the inflow cannula or transcatheter directly points to the mitral valve annulus.

Figure 3:
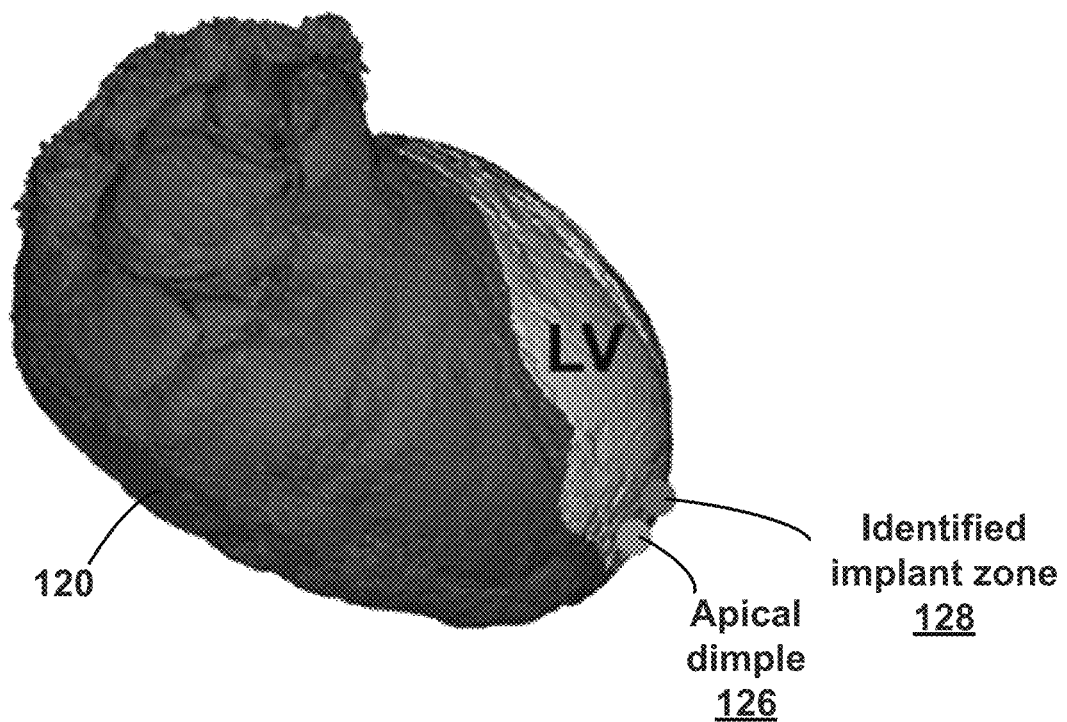
FIG. 3 illustrates a segmented 3D model of a heart showing an apical dimple and an identified implant zone, according to one aspect of the disclosure.

FIG. 3 illustrates a segmented 3D model of a heart showing an apical dimple and an identified implant zone, according to one aspect of the disclosure. In the example of FIG. 3, heart 120 includes apical dimple 126 and identified implant zone 128. In one such example approach, the identified implant zone 128 is positioned relative to the mitral valve annulus 122 of FIG. 2.

Figure 4:
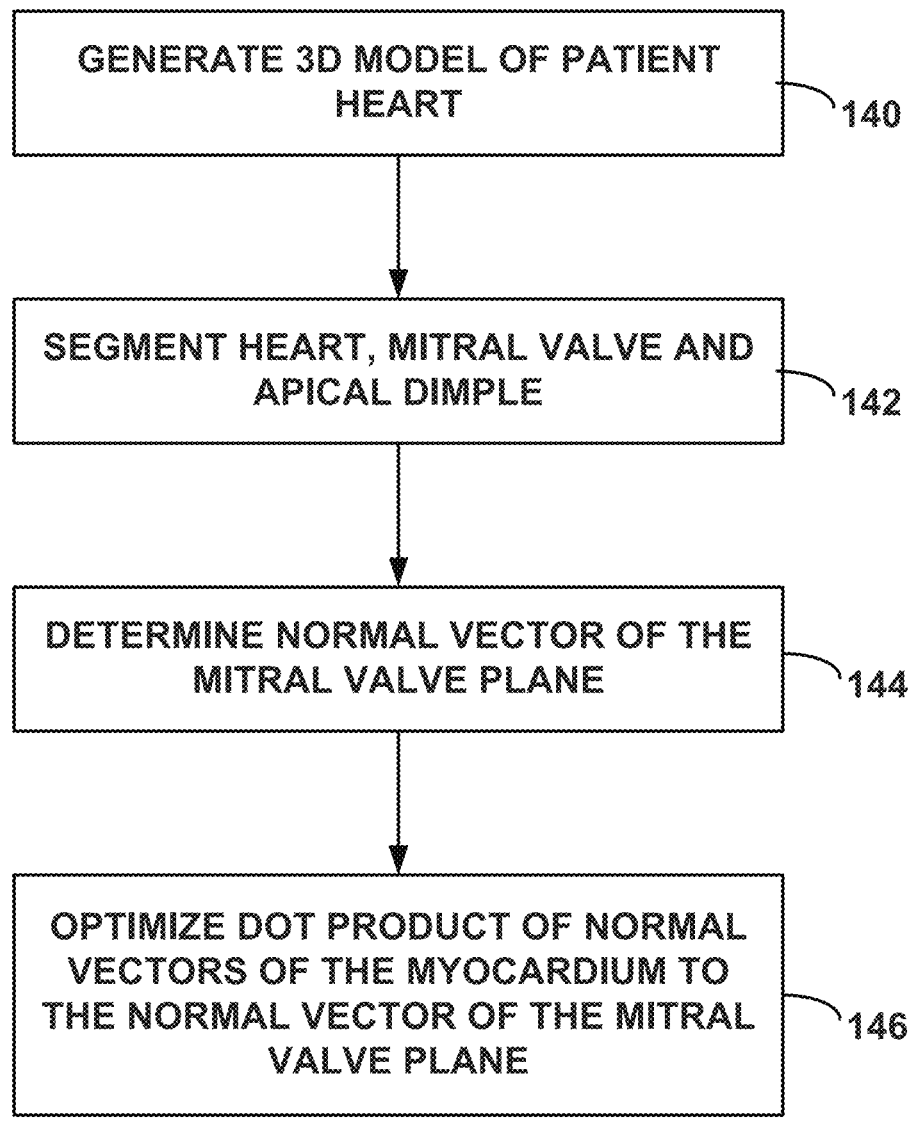
FIG. 4 is a block diagram illustrating another method of determining a LVAD pump implant location, according to one aspect of the disclosure.

FIG. 4 is a block diagram illustrating another method of determining a LVAD pump implant location, according to one aspect of the disclosure. In the example shown in FIG. 4, images of a heart are imported and used to generate a three-dimensional model of a patient's heart (140). The heart, mitral valve and apical dimple are segmented within the image (142) and a vector normal to the mitral valve annulus identified (144). The tool then determines the implant zone by optimizing the dot product of normal vectors of the myocardium to the normal vector of the plane of the mitral valve annulus (146).

Figure 5A:
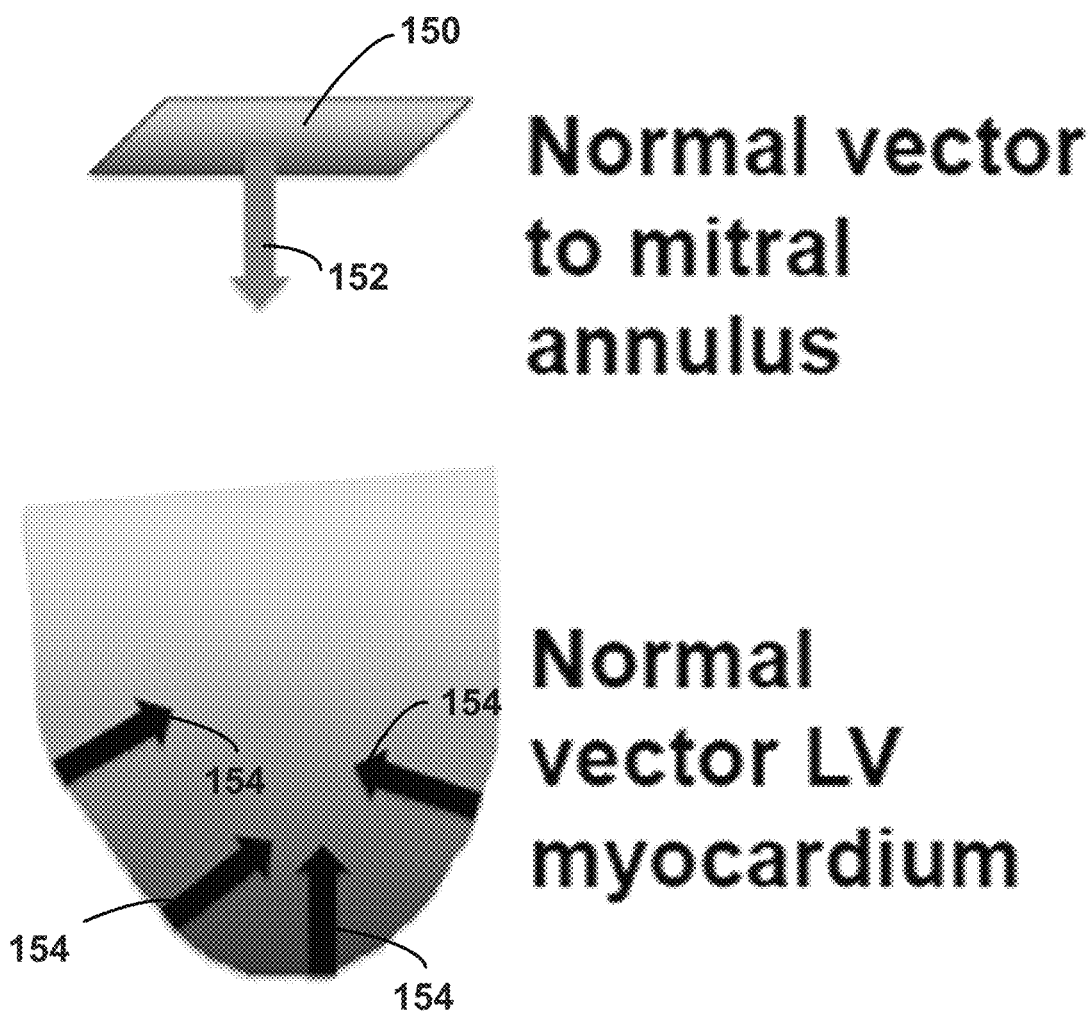
FIGS. 5A and 5B illustrate the method of FIG. 4, according to one aspect of the disclosure.
Figure 5B:
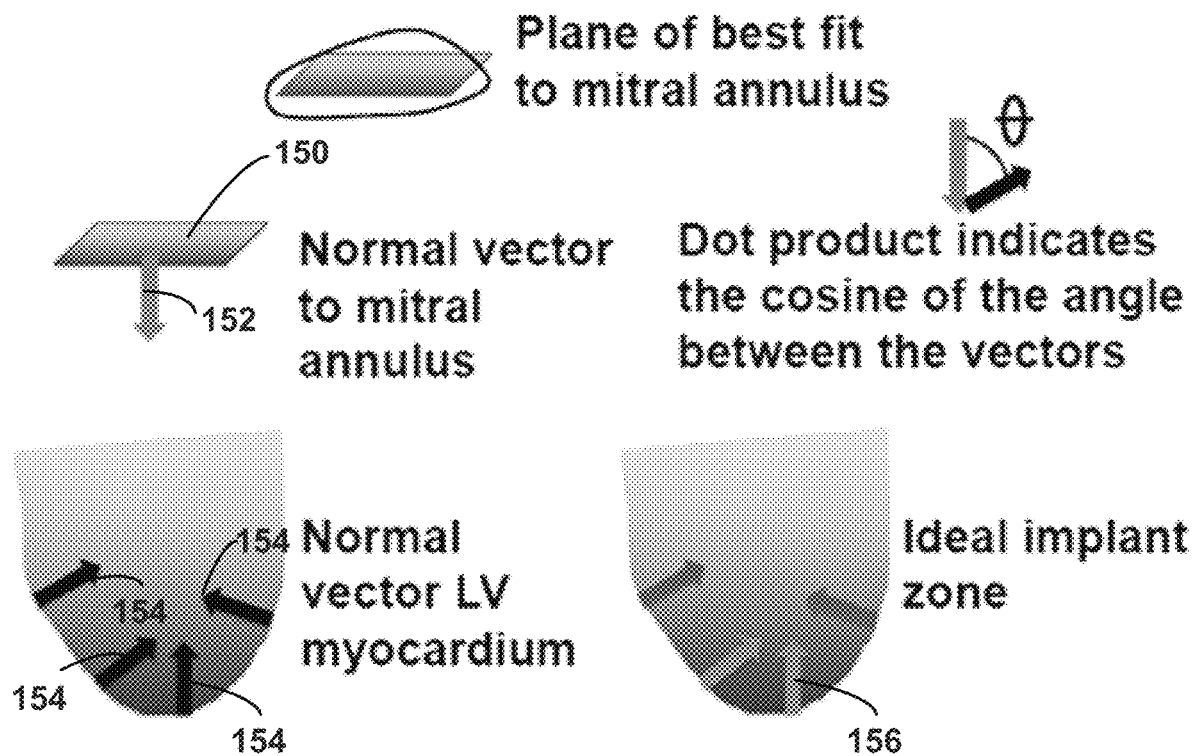
Figure 6:
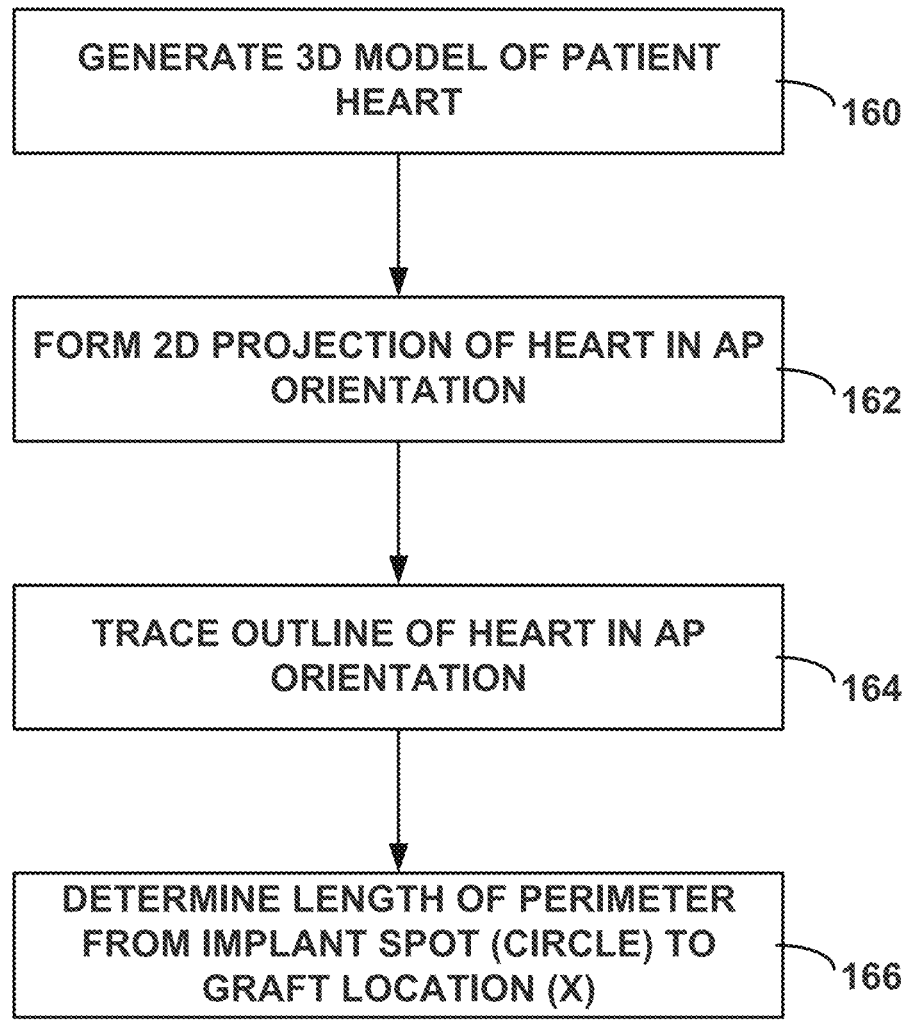
FIGS. 6-10 illustrate a method of determining graft length, according to one aspect of the disclosure.

FIGS. 5A and 5B illustrate the method of FIG. 4, according to one aspect of the disclosure. In the example shown in FIG. 5A, a plane 150 is drawn through the mitral valve annulus and a vector 152 normal to the mitral valve annulus 124 is identified. Vectors 154 normal to the myocardium of the left ventricle are also identified. In the example shown in FIG. 5B, a plane 150 is drawn through the mitral valve annulus and a vector 152 normal to the plane 150 (and normal to the mitral valve annulus 124 is identified. Vectors 154 normal to the myocardium of the left ventricle are also identified and an ideal implant zone 156 identified by optimizing the cosine of the angle between vectors 152 and 154.

Another issue with LVAD implantation is the location and angle of the graft attachment to the aorta. Blood flow entering the aorta should flow in as straight a line as possible through the graft and down into the aorta to minimize turbulence through the connection. It can be difficult to determine the best location to attach the graft to the aorta, and the bevel needed to minimize turbulence.

Figure 7:
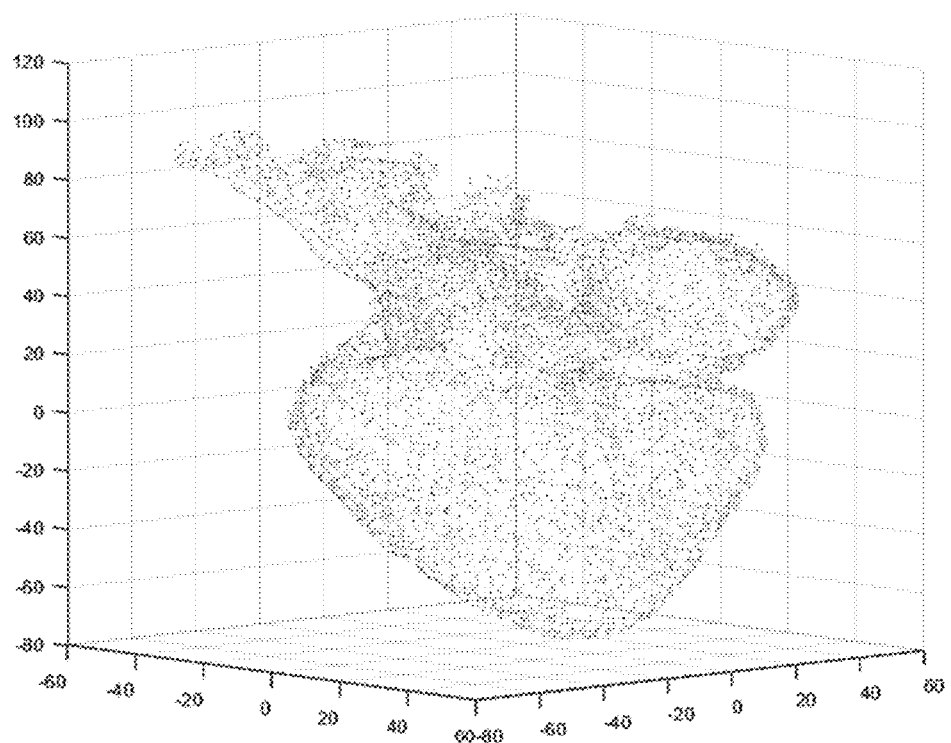

FIGS. 6-10 illustrate a method of determining graft length, according to one aspect of the disclosure. In the example approach shown in FIGS. 6, images of a patient's heart are imported and used to generate a three-dimensional model of the patient's heart (160). In one example approach, as illustrated in FIG. 7, the model may be a point cloud rendering of a 3D mask of the heart model derived from an MRI scan. In another example approach, the model of FIG. 7 may be a point cloud rendering of a heart model derived from another imaging technology, such as CT or ultrasound. The 3D image of the heart is then oriented to generate an anteroposterior view estimated to be the general position of the patient on the operating table, and a 2D projection (FIG. 8) of the 3D model in an anteroposterior position is generated (162). The 2D projection may be used to calculate the perimeter around the patient's heart, providing a hard boundary. In one example approach, the calculated graft path should adhere to but not cross this boundary, essentially following the ideal path for the LVAD implant. In one such approach, an outline of the heart in AP orientation is traced (FIG. 9) (164). The outline is then used to determine the length of the perimeter of the 2D projection from implant spot to graft location (O and X, respectively, in FIG. 10) (166).

In one example approach, the surgeon may be presented with the option to choose the graft end points (overriding the determination of ideal pump implant location and ideal graft connection to the aorta). In such an example approach, the surgeon may select a location on the aorta for the graft connection and a location on the left ventricle for the pump implant.

In one example approach, developers use MRI images of perfusion fixed human hearts to develop a computational tool for determining graft length. In one such example approach, each DICOM image set is imported into Materialise Mimics® and a 3D mask rendering of the attitudinally anatomical heart is created. The 3D mask is then imported into MATLAB where the graft length calculations are performed. A point cloud generated from the matrix may then be used to find the appropriate anatomical landmarks.

LVAD positioning within the patient's chest may be an issue as well. For instance, the septum separating the right ventricle from the left ventricle may fall close to the location a surgeon would typically use to secure the LVAD pump. If the location selected for the pump is incorrect or the angle of the pump is off, the septum may impact blood flowing into the pump, introducing turbulence and potentially damaging the blood cell flowing through the pump.

To address these issues, a method is described for selecting the location of the pump and the length of the graft before surgery. The method processes routine clinical imaging (e.g., chest computed tomography (CT), Magnetic Resonance Imagery (MRI) images, ultrasound techniques such as transthoracic and transesophageal echo, and fluoroscopy) to determine where and how the device should be surgically implanted. In one such approach, virtual segmentation is used to measure the length from the LV apex, the ideal pump location, to the ascending aorta. This should lead to fewer complications and thus a higher success rate for implanting an LVAD.

The techniques described above provide the surgeon with valuable information including the implant location and the graft length needed to minimize device-related adverse events, therefore providing a more repeatable and patient-specific approach to implanting LVAD while improving the clinical success associated with implanting an LVAD.

In some examples, a computer algorithm models where and how the graft should attach to the aorta based on information received from the CT scans. In one such example, implantation planning software determines the best location to attach the graft to the aorta, and the bevel in the graft needed to minimize turbulence. Such an approach reduces turbulence in the blood flow passing from the graft down into the aorta, limiting the damage to the patient's blood cells.

Together, FIGS. 1-10 illustrate a workflow for selecting a location for the LVAD pump and a graft length, according to one aspect of the disclosure. In one example approach, the tool uses pre-procedural CT scans of the patient's cardiothoracic cavity to model the patient's heart, mitral valve, and apical dimple. This information serves as the input to the algorithm.

In one example approach, chest CT or MRI images are collected (FIG. 1) and used to generate a 3D model of the heart (heart 120 in FIG. 3). An ideal implant zone 128 is identified (FIG. 3) in terms of a distance and direction from the apical dimple 126. In one such example approach, the ideal implant zone is determined through the optimization of the dot product between the normal vector of the mitral valve plane and the normal vector of the heart tissue (FIGS. 5A and 5B).

One example approach for determining the location for the LVAD pump itself will be discussed next. In the example approach, the planning software assumes that the implant zone will be where the inflow cannula or transcatheter device points directly to the mitral valve annulus. In one such example approach, images are segmented to create a 3D volume rendering of the left ventricle. The mitral valve annulus and the apical dimple are marked and the locations are uploaded into a program which calculates the angles between the normal vector of the plane representing the mitral annulus and the normal vector of the LV epicardium. The average angles from each area are taken to account for various Fr sizes of catheters or inflow cannula to be positioned. Additionally, the distances between the implant zones and the apical dimples may be calculated. An approximate direction from the dimple to the location for attaching the LVAD may readily be determined visually for a given heart.

Ex vivo echocardiography performed on perfusion fixed human hearts validated this approach. The numerical distances and approximate directions of the ideal implant zones were located relative to the apical dimples. When placing the echo probe at these locations, the mitral valve anatomies were identified. In one example approach, a computational tool successfully determined the implant zone that points toward the center point of the mitral valve annulus. Results seemed feasible comparing the results to ex vivo echocardiography. In one such example approach, the computational approach may be optimized using artificial intelligence (AI) to more quickly reach a solution. In one example approach, the optimal implant site may be co-located with a physical landmark allowing easy application during a given procedure. In one example approach, the computational tool may be modified to be specific to certain LVAD models.

In another example approach for determining the location to implant the LVAD pump, images are segmented to create a 3D volume rendering of the left ventricle. The most lateral point on the LV is selected as the implant location.

In another example approach for determining the location to implant the LVAD pump, images are segmented to create a 3D volume rendering of the left ventricle. The most inferior point on the LV is selected as the implant location.

In another example approach for determining the location to implant the LVAD pump, images are segmented to create a 3D volume rendering of the left ventricle. The most lateral and inferior point on the LV are identified. The midpoint between these points is selected as the implant location.

In another example approach for determining the location to implant the LVAD pump, images are segmented to create a 3D volume rendering of the left ventricle and the corresponding blood volume within the left ventricle. The most inferior point on the blood volume is identified. The point along the LV surface that is closest to the identified point is selected as the implant location.

In another example approach for determining the location to implant the LVAD pump, images are segmented to create a 3D volume rendering of the left ventricle. The most inferior point on the inner surface of the LV is identified. The point along the outer surface of the LV that is closest to the identified point is selected as the implant location.

In another example approach for determining the location to implant the LVAD pump, images are segmented to create a 3D volume rendering of the left ventricle. A best fit paraboloid is created over the surface of the LV. The vertex is selected as the implant location.

In another example approach for determining the location to implant the LVAD pump, images are segmented to create a 3D volume rendering of the left ventricle and the corresponding blood volume within the left ventricle. A best fit paraboloid is created over the blood volume. The vertex is identified. The point along the outer surface of the LV that is closest to the identified point is the implant location.

In another example approach for determining the location to implant the LVAD pump, images are segmented to create a 3D volume rendering of the left ventricle. A best fit paraboloid is created along the inner surface of the LV. The vertex is identified. The point along the outer surface of the LV that is closest to the identified point is the implant location.

Figure 8:
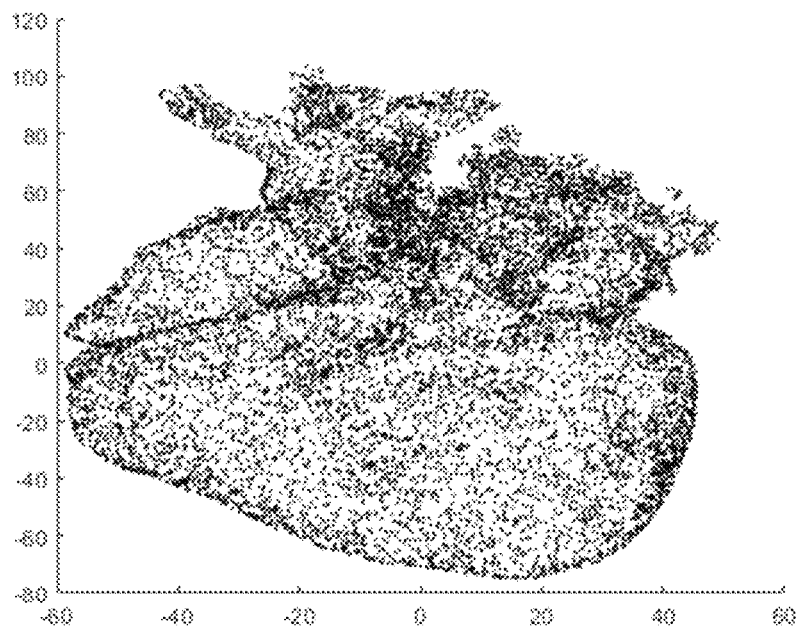
Figure 9:
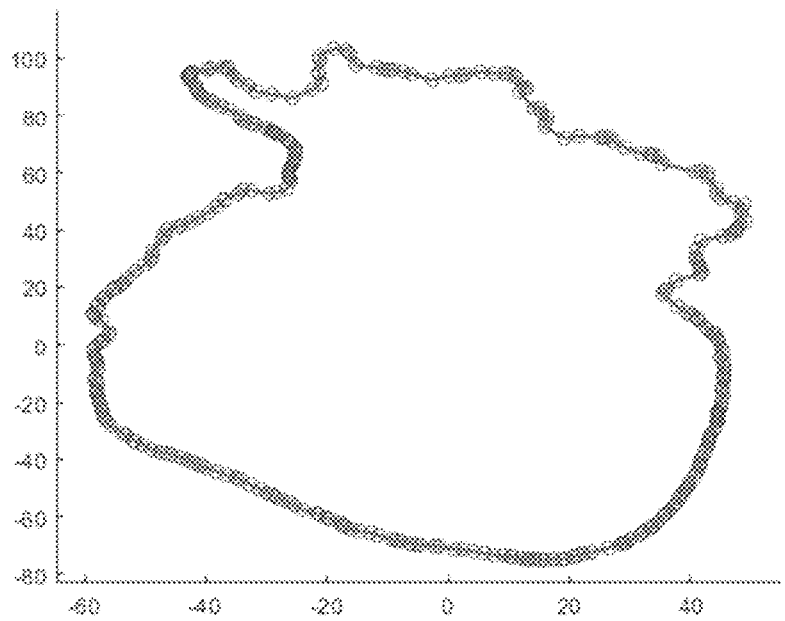
Figure 10:
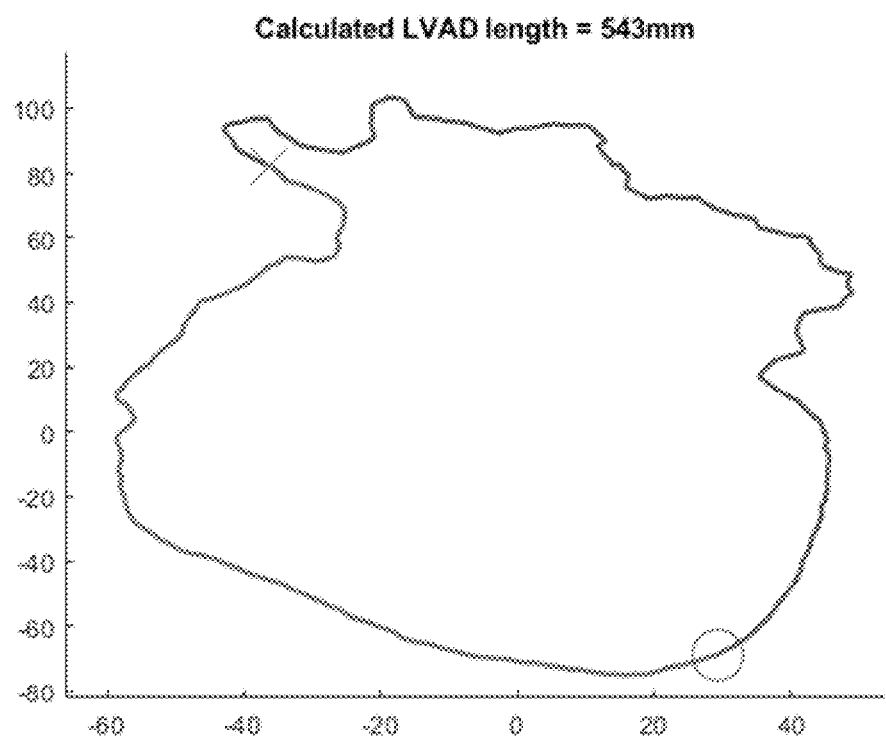

One example approach for determining graft length will be discussed next. In the example approach, the heart tissue is the projected onto a 2D plane (as shown in FIG. 8) and the outline of the 2D image traced (as shown in FIG. 9). The planning software then determines the length of the segment extending from the implant spot (circle) to the graft location (x) as shown in FIG. 10. In some example approaches, curve fitting is used to smooth the perimeter of the projection.

In another example approach for determining graft length, the 3D epicardial surface is mapped. A shortest path algorithm is employed to calculate the distance between the two points (implant spot and graft location).

In another example approach for determining graft length, the margin of the right ventricle is determined based on the 2D projection. This line is mapped into 3D and the distance between the two points is calculated in 3D using the shortest path algorithm. Determine margin of RV in 2D, passing through the line.

In another example approach for determining graft length, a third point is determined that is orthogonal to the two end points and a best fit curve is created through the three points.

In one example approach, planning software selects a location on the aorta to be used to attach the graft, and a bevel for the graft used to attach to the selected location. In one such example approach, the planning software models blood flow through the aorta and attempts select a location and bevel needed to match the direction of blood flow. In one such example approach, a location for attachment to the aorta and a corresponding bevel for the graft is then selected to minimize turbulence in blood flow through the blood vessel. Such an approach limits reduces in the blood cells passing through the aorta.

Figure 11:
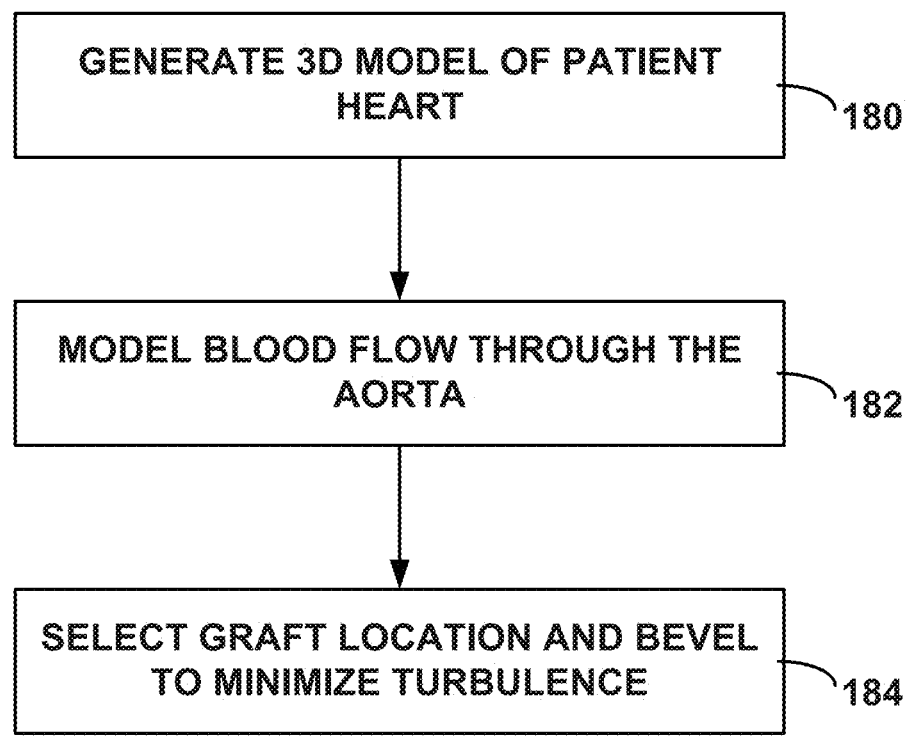
FIG. 11 is a block diagram illustrating a method for determining the location and bevel of a graft connection to the aorta, in accordance with one of the aspects of the disclosure.

FIG. 11 is a block diagram illustrating a method for determining the location and bevel of a graft connection to the aorta, in accordance with one of the aspects of the disclosure. In one example approach, blood flow through the aorta is simulated based on the model generated from the CT or MRI images and fluid modeling software is used to model the turbulence added when connecting the graft at the selected location and bevel angle. In the example shown in FIG. 11, images of a patient's heart are imported and used to generate a three-dimensional model of the patient's heart (180). The method models blood flow through the aorta (182) and attempts to select a graft attachment location and bevel needed to match the direction of blood flow and minimize turbulence (184).

In another example approach, the planning software uses the upper vasculature landmarks, including but not limited to the right brachiocephalic artery, the left common carotid, and the left subclavian artery, to select a location that is a fixed, specified distance from this anatomy.

In another example approach, the planning software uses the coronary arteries to select a location that is a fixed, specified distance from this anatomy.

In another example approach, the planning software fits the ascending aorta to a curve. The selected location is a specified point along this curve.

In one example approach, the output of the planning software is an attachment location on the aorta, an implant location and a graft length. This information is relayed to the surgeon before the procedure. In some example approaches, the planning software allows the surgeon to select one or more of the attachment location on the aorta, the implant location for the LVAD and the graft length. In some example approaches, the planning software allows the surgeon to constrain the location of one or more of the attachment location on the aorta and the implant location for the LVAD to specific areas on the heart model. In some example approaches, the planning software allows the surgeon to constrain the allowable lengths of the graft.

In trials, the computational tool successfully determined the implant zone that points toward the center point of the mitral valve annulus. Results were feasible comparing the results to ex vivo echocardiography. In one example approach, a computational approach may be optimized utilizing AI and results obtained within seconds. The optimal implant site may be readily co-located with a physical landmark allowing easy application during a given procedure.

A method of attaching an assist device to a blood vessel will be discussed next. In one example approach, CT or MRI images are collected and used to generate a model of the blood vessel. A location for attachment to the blood vessel and corresponding bevel for the graft is then selected to minimize turbulence in blood flow through the blood vessel.

Figure 12:
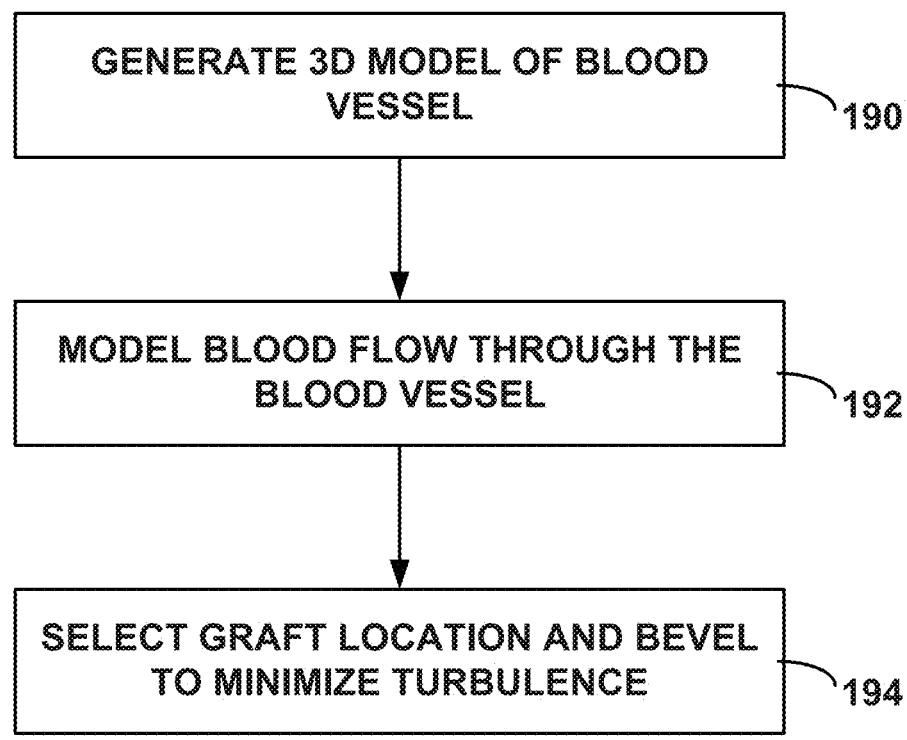
FIG. 12 is a block diagram illustrating a method for determining the location and bevel of a graft connection to a blood vessel, in accordance with one of the aspects of the disclosure.

FIG. 12 is a block diagram illustrating a method for determining the location and bevel of a graft connection to a blood vessel, in accordance with one of the aspects of the disclosure. In one example approach, blood flow through the blood vessel is simulated based on the model generated from the CT or MRI images and fluid modeling software is used to model the turbulence added when connecting the graft at the selected location and bevel angle. In the example shown in FIG. 12, images of a patient's heart are imported and used to generate a three-dimensional model of the patient's blood vessel (190). The method models blood flow through the blood vessel when a graft is attached (192) and attempts to select a location and bevel needed to match the direction of blood flow and minimize turbulence (194).

Various other cardiac procedures require device insertions through the LV apex. It can be clinically difficult to determine the ideal location of incisions, because in some cases physicians only have external views of the given heart. Physicians may, for instance, palpate for the apical dimple. The approaches described herein locate a near optimal implant zone for patient-specific anatomies. The methods discussed above may, therefore, also be used in other medical procedures. For instance, the approach may be used as discussed above to determine a graft location and graft bevel angle for attachment of grafts to blood vessels in other areas of the body. In addition, procedures such as mitral valve replacements and chordal repairs may benefit from a similar workflow and algorithm.

The present techniques may be used, for instance, to reuse grafts that have fibrosed into the aorta. One model LVAD may, for instance, be replaced with a different or newer model and the graft position and length modeled to reuse the current graft.

Figure 13:
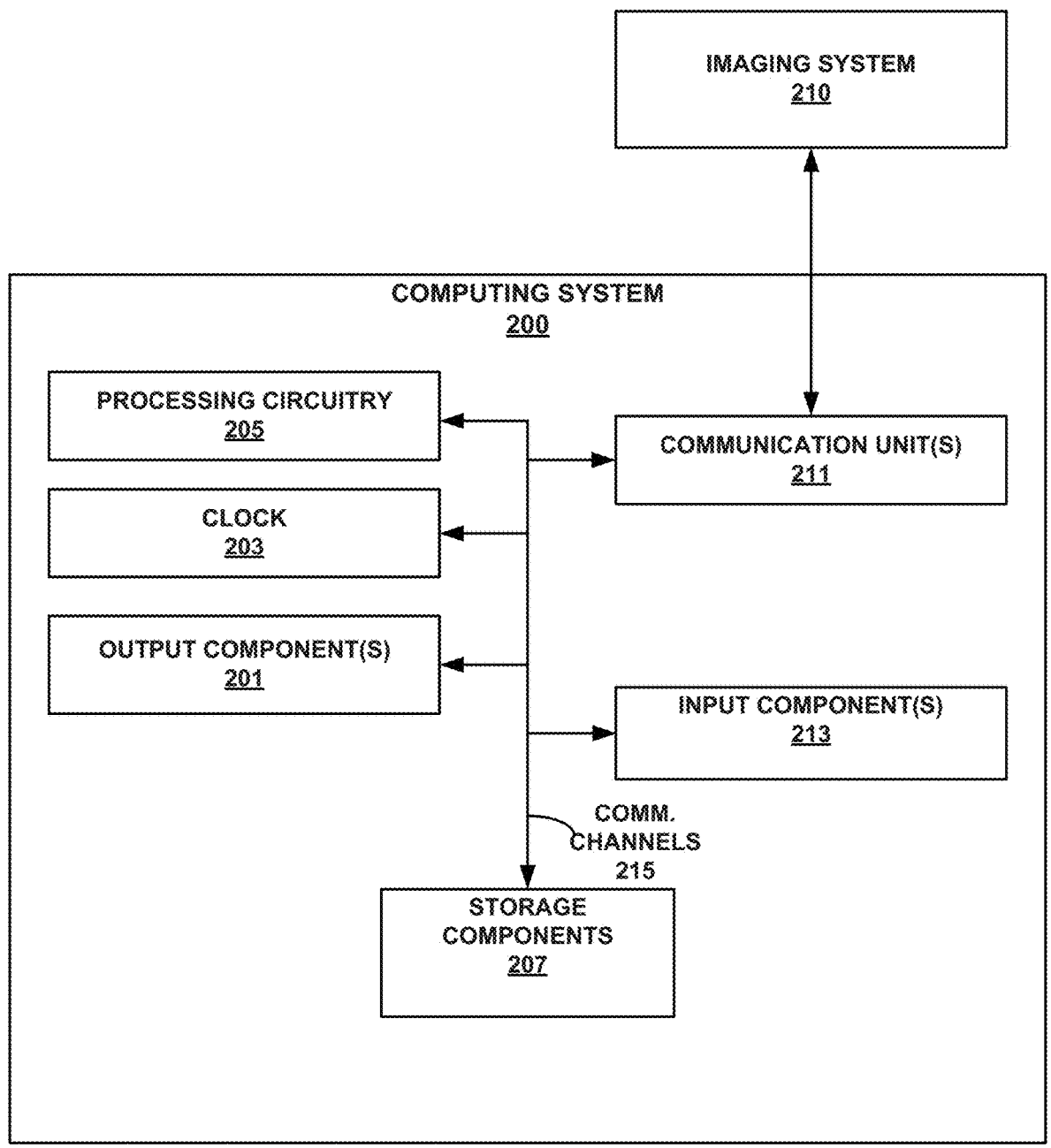
FIG. 13 illustrates one example of a computing system used to execute the techniques of FIGS. 1-12, in accordance with one or more techniques of the disclosure.

FIG. 13 illustrates one example of a computing system used to execute the techniques illustrated in FIGS. 1-12, in accordance with one or more techniques of the disclosure. Other examples of computing system 200 may be used in other instances and these examples may include a subset of the components included in example computing system 200 or may include additional components not shown in example computing system 200 of FIG. 13.

As shown in the example of FIG. 13, computing system 200 includes processing circuitry 205, one or more input components 213, one or more communication units 211, one or more output components 201, and one or more storage components 207. Communication channels 215 may interconnect each of the components 201, 203, 205, 207, 211, and 213 for inter-component communications (physically, communicatively, and/or operatively). In some examples, communication channels 215 may include a system bus, a network connection, an inter-process communication data structure, or any other method for communicating data.

One or more communication units 211 of computing system 200 may communicate with external devices, such an imaging system 210, via one or more wired and/or wireless networks by transmitting and/or receiving network signals on the one or more networks. In some examples, imaging system 210 provides pre-procedural or intra-procedural images for processing as described above. Examples of communication units 211 include a network interface card (e.g., such as an Ethernet card), an optical transceiver, a radio frequency transceiver, a GPS receiver, or any other type of device that can send and/or receive information. Other examples of communication units 211 may include short wave radios, cellular data radios, wireless network radios, as well as universal serial bus (USB) controllers. Examples of imaging systems 210 include computed tomography (CT) systems, Magnetic Resonance Imagery (MRI) systems, ultrasound systems such as transthoracic and transesophageal echo, and fluoroscopy systems.

One or more input components 213 of computing system 200 may receive input. Examples of input are tactile, audio, and video input. Input components 213 of computing system 200, in one example, includes a presence-sensitive input device (e.g., a touch sensitive screen), mouse, keyboard, voice responsive system, video camera, microphone or any other type of device for detecting input from a human or machine. In some examples, input components 213 may include one or more sensor components one or more location sensors (GPS components, Wi-Fi components, cellular components), one or more temperature sensors, one or more movement sensors (e.g., accelerometers, gyroscopes), one or more pressure sensors (e.g., barometer), one or more ambient light sensors, and one or more other sensors (e.g., microphone, camera, infrared proximity sensor, hygrometer, and the like).

One or more output components 201 of computing system 200 may generate output. Examples of output are tactile, audio, and video output. Output components 201 of computing system 200, in one example, includes a sound card, video graphics adapter card, speaker, liquid crystal display (LCD), or any other type of device for generating output to a human or machine.

Processing circuitry 205 may implement functionality and/or execute instructions associated with computing system 200. Examples of processing circuitry 205 include application processors, display controllers, auxiliary processors, one or more sensor hubs, and any other hardware configure to function as a processor, a processing unit, or a processing device. Processing circuitry 205 of computing system 200 may retrieve and execute instructions stored by storage components 207 that cause processing circuitry 205 to perform operations for processing image data as described above. The instructions, when executed by processing circuitry 205, may cause computing system 200 to store information within storage components 207.

One or more storage components 207 within computing system 200 may store information for processing during operation of computing system 200. In some examples, storage component 207 includes a temporary memory, meaning that a primary purpose of one example storage component 207 is not long-term storage. Storage components 207 on computing system 200 may be configured for short-term storage of information as volatile memory and therefore not retain stored contents if powered off. Examples of volatile memories include random-access memories (RAM), dynamic random-access memories (DRAM), static random-access memories (SRAM), and other forms of volatile memories known in the art.

Storage components 207, in some examples, also include one or more computer-readable storage media. Storage components 207 in some examples include one or more non-transitory computer-readable storage mediums. Storage components 207 may be configured to store larger amounts of information than typically stored by volatile memory. Storage components 207 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage components 207 may include a memory configured to store data or other information associated with heart or blood vessel imaging or modelling, graft length or graft or pump implant location.

Clock 203 is a device that allows computing system 200 to measure the passage of time (e.g., track system time). Clock 203 typically operates at a set frequency and measures a number of ticks that have transpired since some arbitrary starting date. Clock 203 may be implemented in hardware or software.

Pre-operative imaging is already in use for LVAD implantation procedures. It is imperative, therefore, to attempt to use this information to ensure improved outcomes. Outflow graft sizing, pump implant location, and graft connection to the aorta (including anastomosis angle) may best be determined by computation techniques, increasing reliability and reproducibility.

The techniques discussed above may be applied in robotic surgery to determine the location and orientation of the LVAD device, the point where the pump is connected to the heart and the length and positioning of the graft. In some example approaches, the locations selected may be overridden by the surgeon.

In one or more examples, the algorithms, operations and functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), and Blu-ray disc, where disks usually reproduce data magnetically, while discs reproduce data optically with lasers. Combinations of the above should also be included within the scope of computer-readable media.

The invention claimed is:

1. A method of planning implantation of a heart assist device, the method comprising:
   accessing, by processing circuitry, images of the cardiothoracic cavity of a patient;
   forming, by the processing circuitry and based on the images, a model of the heart of the patient, the model including a model of a mitral valve annulus;
   determining, by the processing circuitry, a normal vector to the mitral valve annulus;
   identifying, by the processing circuitry, an apical region;
   determining, by the processing circuitry, a plurality of myocardium vectors normal to respective locations on a myocardium of the heart;
   determining, by the processing circuitry, a plurality dot products of respective myocardium vectors of the plurality of myocardium vectors to the normal vector to the mitral valve annulus;
   selecting, by the processing circuitry and based on the plurality of dot products, an insertion point for implanting the heart assist device within the apical region;
   controlling, by the processing circuitry, a display to present the insertion point on the model of the heart; and
   controlling a robot during robotic surgery to implant the heart assist device according to the insertion point.

2. The method of claim 1, wherein the insertion point is selected to point at the mitral valve annulus.

3. The method of claim 1, wherein selecting the insertion point comprises selecting the insertion point according to a minimum dot product of the plurality of dot products.

4. The method of claim 1, wherein the model includes a left ventricle, the apical region being on the left ventricle.

5. The method of claim 4, wherein the model includes a model of blood volume within the left ventricle.

6. The method of claim 4, wherein the model includes a three-dimensional (3D) volume rendering of the left ventricle.

7. The method of claim 1, wherein the model includes a model of an aorta and wherein the method further includes:
   selecting a graft location on the aorta; and
   calculating the graft length as a function of the selected insertion point and the selected graft location.

8. The method of claim 7, wherein selecting the graft location on the aorta includes selecting a location for the graft that matches the direction of blood flow from the graft to the direction of blood flow through the aorta.

9. The method of claim 7, wherein selecting a graft location on the aorta includes selecting a location and a bevel for the graft that matches the direction of blood flow from the graft to the direction of blood flow through the aorta.

10. The method of claim 7, wherein calculating the graft length as a function of the insertion point and the selected graft location includes:
    projecting an image of the heart onto a two-dimensional plane based on the model; and
    tracing an outline of the projected heart image.

11. A method of determining the length of a graft used for implanting a left ventricular assist device (LVAD) in a patient, the method comprising:
    accessing, by processing circuitry, images of the cardiothoracic cavity of the patient;
    forming, by the processing circuitry, a model of the heart of the patient;
    determining, by the processing circuitry and based on the model of the heart, a normal vector to a mitral valve annulus of the heart;
    determining, by the processing circuitry, a plurality dot products of a plurality of vectors normal to a myocardium of the heart to the normal vector to the mitral valve annulus;
    determining, by the processing circuitry and based on the plurality of dot products, an implant location;
    selecting, by the processing circuitry, a graft location on an aorta;
    calculating, by the processing circuitry, the graft length as a function of the implant location and the selected graft location;
    controlling, by the processing circuitry, a display to present the implant location on the model of the heart and to present the graft length; and
    controlling a robot during robotic surgery to implant the heart assist device according to the insertion point.

12. The method of claim 11, wherein calculating the graft length as a function of the implant location and the selected graft location includes:
    projecting an image of the heart onto a two-dimensional plane based on the model; and
    tracing an outline of the projected heart image.

13. A system, comprising:
    memory; and
    one or more processors connected to the memory, wherein the memory includes instructions that, when executed by the one or more processors, cause the system to:
access images of the cardiothoracic cavity of a patient;
form, based on the images, a model of the heart of the patient, the model including a model of a mitral valve annulus;
determine a normal vector to the mitral valve annulus;
identify an apical region;
determine a plurality of myocardium vectors normal to respective locations on a myocardium of the heart;
determine a plurality dot products of respective myocardium vectors of the plurality of myocardium vectors to the normal vector to the mitral valve annulus;
select, based on the plurality of dot products, an insertion point for a heart assist device based on the model;
control a display to present the insertion point on the model of the heart, and
control a robot during robotic surgery to implant the heart assist device according to the insertion point.

14. A system, comprising:
memory; and
one or more processors connected to the memory,
wherein the memory includes instructions that, when executed by the one or more processors, cause the system to:
access images of the cardiothoracic cavity of a patient;
form, based on the images, a model of the heart of the patient;
determine, based on the model of the heart, a normal vector to a mitral valve annulus of the heart;
determine a plurality of myocardium vectors normal to respective locations on a myocardium of the heart;
determine a plurality dot products of respective myocardium vectors of the plurality of myocardium vectors to the normal vector to the mitral valve annulus;
select, based on the plurality of dot products, an insertion point for a heart assist device based on the model of the heart;
select a graft location on a aorta;
calculate a graft length as a function of the insertion point and the selected graft location;
control a display to present the insertion point on the model of the heart and to present the graft length; and
control a robot during robotic surgery to implant the heart assist device according to the insertion point.

15. The system of claim 14, wherein the instructions that, when executed by the one or more processors, cause the system to calculate the graft length as a function of the insertion point and the selected graft location includes instructions that, when executed by the one or more processors, cause the system to:
project an image of the heart onto a two-dimensional plane based on the model; and
trace an outline of the projected heart image.

* * * * *